(12) United States Patent
Ghiassi et al.

(10) Patent No.: US 11,319,421 B1
(45) Date of Patent: May 3, 2022

(54) MICROFLUIDIC FLOW PROCESS FOR MAKING MONOMERS

(71) Applicant: Government of the United States, as represented by the Secretary of the Air Force, Wright-Patterson AFB, OH (US)

(72) Inventors: Kamran B Ghiassi, Palmdale, CA (US); Neil D Redeker, Lancaster, CA (US); Alexander T Lonnecker, Lancaster, CA (US); Jayden N. Glover, Fort Collins, CO (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 301 days.

(21) Appl. No.: 16/658,489

(22) Filed: Oct. 21, 2019

(51) Int. Cl.
*B01J 19/00* (2006.01)
*B01J 19/24* (2006.01)
*C08J 5/24* (2006.01)
*C08G 73/06* (2006.01)
*C07C 261/02* (2006.01)

(52) U.S. Cl.
CPC ............ *C08J 5/24* (2013.01); *B01J 19/0093* (2013.01); *C07C 261/02* (2013.01); *C08G 73/065* (2013.01); *C08J 2379/04* (2013.01)

(58) Field of Classification Search
CPC ........ B01J 19/00; B01J 19/0093; B01J 19/24; C07C 261/00; C07C 261/02; C08G 73/00; C08G 73/06; C08G 73/0622; C08G 73/0638; C08G 73/065; C08J 5/00; C08J 5/24; C08J 2379/00; C08J 2379/04
See application file for complete search history.

(56) References Cited

U.S. PATENT DOCUMENTS 3,107,261 A    10/1963    Gerber et al.
3,553,255 A    1/1971    Grigat et al.
(Continued)

OTHER PUBLICATIONS

Adamo, A; Beingessner,R. L.; B; Ehnam, M.; Chen, J.; Jamison, T. F.; Jensen, K. F.; Monbaliu, J. M.; Myerson, A. S.; Revalor, E. M.; Snead, D. R.; Stelzer, T.; Weeranoppanant, N.; Shin Yee Wong, S. Y.; Ping Zhang, P.; On-demand continuous-flow production of pharmaceuticals in a compact, reconfigurable, Science 352 (6281), 61-67, 2016.

(Continued)

*Primary Examiner* — Natasha E Young
(74) *Attorney, Agent, or Firm* — AFMCLO/JAZ; James F McBride

(57) ABSTRACT

The present invention relates to a microfluidic flow process for making monomers, monomers made by such processes, and methods of using such monomers. In such process, microfluidic reaction technology is used to synthesize cyanation reaction products orders of magnitude faster than is possible in batch and continuous syntheses. The aforementioned process does require strictly regulated, highly toxic cyanogen chloride. Thus the aforementioned process is more economically efficient and reduces the environmental impact of thermosetting resin monomer production, and produces thermosetting resin monomers in greater purity than obtained through typical processes.

16 Claims, 2 Drawing Sheets

(56) References Cited

U.S. PATENT DOCUMENTS

| | | | | |
|---|---|---|---|---|
| 4,731,420 | A | * 3/1988 | Hefner, Jr. | ............. C08G 59/04 |
| | | | | 525/404 |
| 4,981,994 | A | * 1/1991 | Jackson | ................ C07C 261/02 |
| | | | | 560/301 |
| 5,420,342 | A | 5/1995 | Craig | |
| 5,756,592 | A | 5/1998 | Bedwell et al. | |
| 6,603,035 | B1 | 8/2003 | Okamoto et al. | |
| 8,546,468 | B2 * | 10/2013 | Mattmann | ............. C08F 220/06 |
| | | | | 523/351 |
| 9,169,356 | B2 | 10/2015 | Sugano et al. | |

OTHER PUBLICATIONS

Liang, H.; Yujun Song, Y.; Microfluidics: Fundamentals, Devices and Applications, First Edition. 11 Microfluidic Synthesis of Organics 2018, 351-374.

Brandon J. Reizman, B. J.; Klavs F. Jensen, K. F.; An Automated Continuous-Flow Platform for the Estimation of Multistep Reaction Kinetics, Org. Process Res. Dev. 2012, 16, 1770-1782.

Sahoo, H. R.; Kralj, J. G.; Jensen, K. F.; Multistep Continuous-Flow Microchemical Synthesis Involving Multiple Reactions and Separations, Angew. Chem. Int. Ed. 2007, 46, 5704-5708.

Laskoski, M.; Dominguez, D. D.;Keller, T. M.; Synthesis and Properties of a Liquid Oligomeric Cyanate Ester Resin, Polymer, 2006, 47, 3727-373.

* cited by examiner

US 11,319,421 B1

MICROFLUIDIC FLOW PROCESS FOR MAKING MONOMERS

RIGHTS OF THE GOVERNMENT

The invention described herein may be manufactured and used by or for the Government of the United States for all governmental purposes without the payment of any royalty.

FIELD OF THE INVENTION

The present invention relates to a microfluidic flow process for making monomers, monomers made by such processes, and methods of using such monomers.

BACKGROUND OF THE INVENTION

Cyanation reactions are commonly used to produce monomers used in the production of thermosetting cyanate ester materials via batch and continuous processes. Unfortunately, conventional production processes are difficult to scale up, inefficient at high rates of production and result in monomer batches that contain impurities, which typically require expensive and/or environmentally unfriendly solvent assisted purification steps to remove. These impurities may be avoided through the use of the strictly regulated, highly toxic cyanogen chloride; however environmental regulations make it extremely difficult, time consuming and expensive to both purchase and use this substance.

Applicants recognized that the inefficiencies associated with the aforementioned conventional production processes arise from the lack of precise temperature control and uniformity in the reaction mixture which in turn leads to the formation of significant quantities of impurities. Therefore, Applicants recognized that a new synthetic method that utilizes low reaction temperatures to suppress side-product formation while incorporating high reactor throughput to maximize production would be advantageous to the manufacturing of uncontaminated cyanate ester resins.

Applicants discovered that such problems could be minimized by conducting cyanation reactions in a microfluidic flow regime. While not being bound by theory, Applicants believe that employing a microfluidic flow regime addresses the aforementioned processing challenges as microfluidic flow reaction cells, i.e. reaction channels that are typically below 500 µm in diameter, have surface to volume ratios three to four orders of magnitude greater than a typical benchtop scale reaction and plant sized batch reactor respectively, and two to three orders of magnitude greater than a typical production scale continuous reactor. Therefore, microfluidic flow reactors possess efficient mixing that is not possible in conventional processes, and may leverage this efficiency to utilize short residence times. Furthermore, microfluidic reactors possess excellent heat transfer which can be utilized to run the reaction at temperatures and production rates not concurrently possible in conventional processes due to the exothermic nature of the cyanation. As a result, local hot spots and concentration gradients in batch reactors and continuous processes are common root causes of poor reaction selectivity, formation of byproducts and unwanted side reactions. Furthermore, Applicants recognized that since microfluidic flow reactions are scaled out instead of scaled up, a single set of reaction conditions can be used to produce small bench-top quantities of material, pilot-plant scale quantities of material and even full scale production quantities of material without the significant process development that is required for conventional cyanation processes. Thus, the reaction conditions used for synthesis of gram-scale quantities of material can be used to make many kilograms of monomer for the production of articles.

SUMMARY OF THE INVENTION

The present invention relates to a microfluidic flow process for making monomers, monomers made by such processes, and methods of using such monomers. In such process, microfluidic reaction technology is used to synthesize cyanation reaction products orders of magnitude faster than is possible in batch and continuous syntheses. The aforementioned process does not require strictly regulated, highly toxic cyanogen chloride. Thus the aforementioned process is more economically efficient and reduces the environmental impact of thermosetting resin monomer production, and produces thermosetting resin monomers in greater purity than obtained through typical processes.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Definitions

Figure 1:
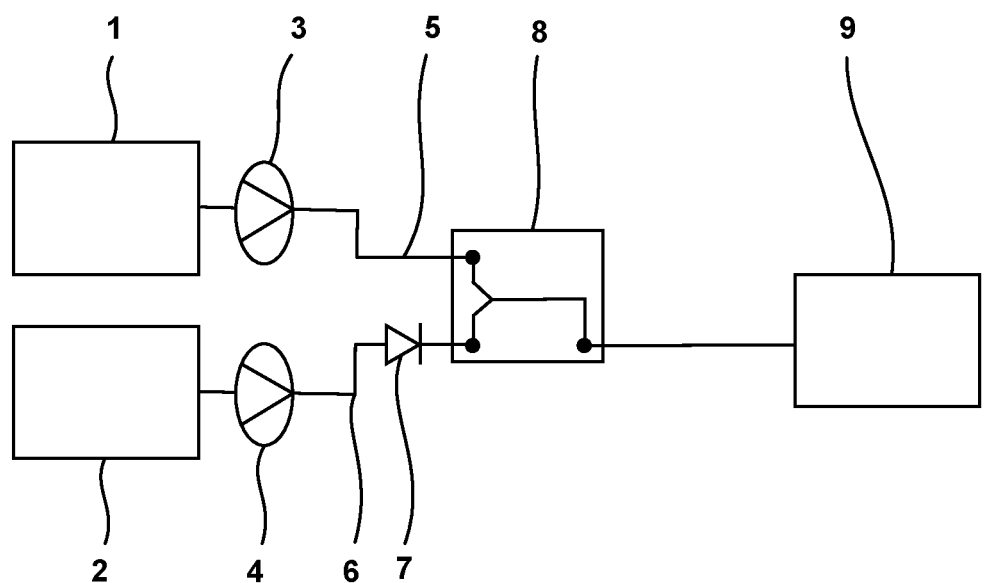
FIG. 1 is a schematic displaying a flow reactor system that employs a chip style reactor design.

Unless specifically stated otherwise, as used herein, the terms "a", "an" and "the" mean "at least one".

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Processes of Making Monomers

For purposes of this specification, headings are not considered paragraphs and thus this paragraph is Paragraph 0016 of the present specification. The individual number of each paragraph above and below this paragraph can be determined by reference to this paragraph's number. In this Paragraph 0016, Applicants disclose a process of making a monomer said process comprising processing, in a microfluidic reactor the following materials:
a) a multifunctional phenol;
b) a cyanogen halide, preferably said cyanogen halide comprises a chloride cyanogen and/or cyanogen bromide, more preferably said cyanogen halide is a chloride cyanogen and/or cyanogen bromide; and
c) a base selected from the group consisting of an organic base, an inorganic base and mixtures thereof;
at a temperature of from about −78° C. to about 25° C., said materials' having residence time of from about 0.1 seconds to about 600 seconds.

Applicants disclose a process according to Paragraph 0016, wherein said temperature is from about −78° C. to about 0° C., preferably said temperature is from about −40° C. to about −10° C. and said residence time is from about 1 second to about 80 seconds, preferably said residence time is from about 20 second to about 30 seconds or said residence time is from about 1 second to about 10 seconds. When said residence time is from about 20 second to about 30 seconds a packed bed microfluidics reactor maybe be used and when said residence time from about 1 second to about 10 seconds an etched canal chipped microreactor may be used.

The process according to Paragraphs 0016 through 0017, wherein said processing comprising:
a) combining:
  (i) a first solution comprising a material selected from the group consisting of a multifunctional phenol; and a base selected from the group consisting of an organic base, an inorganic base and mixtures thereof; and
  (ii) a second solution comprising a cyanogen halide, preferably said cyanogen halide comprises a chloride cyanogen and/or cyanogen bromide, more preferably said cyanogen halide is a chloride cyanogen and/or cyanogen bromide;
b) combining
  (i) a first solution comprising a multifunctional phenol; a cyanogen halide, preferably said cyanogen halide comprises a chloride cyanogen and/or cyanogen bromide, more preferably said cyanogen halide is a chloride cyanogen and/or cyanogen bromide; acetonitrile and an optional aprotic co-solvent; and
  (ii) a base selected from the group consisting of an organic base, an inorganic base and mixtures thereof with the proviso that when said base is a solid base, said solid base is dissolved in a liquid prior to combining said solid base with said first solution; or
c) simultaneously combining a first solution comprising multifunctional phenol, acetonitrile and an optional aprotic co-solvent; a second solution comprising a cyanogen halide, preferably said cyanogen halide comprises a chloride cyanogen and/or cyanogen bromide, more preferably said cyanogen halide is a chloride cyanogen and/or cyanogen bromide, and an aprotic solvent; and a third solution comprising a base selected from the group consisting of an organic base, an inorganic base and mixtures thereof with the proviso that when said base is a solid base, said solid base is dissolved in a liquid prior to combining said solid base with said first solution, and an optional aprotic solvent.

The process according to Paragraphs 0016 through 0017, wherein:
a) said multifunctional phenol is selected from the group consisting a 1,4-benzenediol, 1,3-benzenediol, 1,2-benzenediol, 2,2-Bis(4-hydroxyphenyl)propane, 1,1-Bis(4-hydroxyphenyl)ethane, 2,2-Bis(4-hydroxy-3-methylphenyl)propane, 2,2-Bis(4-hydroxyphenyl)hexafluoropropane, 3,4',5-Trihydroxy-trans-stilbene 3,4',5-Trihydroxy-cis-stilbene, 1,1-Bis(4-hydroxyphenyl)sulfone, phenylbis(4-hydroxyphenyl)phosphine oxide, phenylbis(3-hydroxyphenyl)phosphine oxide, tris(3-hydroxyphenyl)phosphine oxide, and mixtures thereof, preferably said multifunctional phenol is selected from the group consisting of 2,2-Bis(4-hydroxyphenyl)propane, 1,1-Bis(4-hydroxyphenyl)ethane, 3,4',5-Trihydroxy-trans-stilbene, 3,4',5-Trihydroxy-cis-stilbene and mixtures thereof;
b) said cyanogen halide is selected from the group consisting of cyanogen chloride, cyanogen bromide and mixtures thereof, preferably said cyanogen halide comprises cyanogen bromide;
c) said inorganic base is selected from the group consisting sodium hydroxide, lithium hydroxide, and mixtures thereof;
d) said organic base is selected from the group consisting of tetraalkyl ammonium hydroxides, preferably tetramethylammonium hydroxide or tetrabutylammonium hydroxide; N-methyl pyrrolidine; a trialkyl amine, preferably triethylamine, tributyl amine, or diethylmonopropylamine; N-methyl pyrollidine; N,N-dialkylanilines, preferably N,N-diethylaniline or N,N-dimethylaniline; and N-methyl piperidine; preferably said organic base is selected from the group consisting of triethylamine, tetrabutylammonium hydroxide, sodium phenoxide and mixtures thereof, most preferably said organic base is selected from the group consisting of sodium phenoxide or triethylamine and mixtures thereof.

The process according to Paragraph 0019, wherein:
a) said multifunctional phenol comprises 1,1-Bis(4-hydroxyphenyl)ethane;
b) said base comprises sodium hydroxide and/or triethylamine; and
c) said solvent is selected from the group consisting of dichloromethane, acetonitrile and mixtures thereof.

A co-solvent such as tetrahydrofuran may be used in combination with dichloromethane and/or acetonitrile when a component, for example, said multifunctional phenol is not readily soluble in dichloromethane and/or acetonitrile.

The process according to Paragraphs 0016 through 0020 comprising a cyanation reaction.

The process according to Paragraphs 0016 through 0021 wherein said monomer is a cyanation reaction product.

A process of producing an article, producing a monomer according to Paragraphs 0016 through 0022 and applying said monomer to said substrate or applying a monomer produced according to Paragraphs 0016 through 0022 to said substrate and polymerizing said monomer after said monomer is applied to a substrate, preferably said substrate comprises carbon fiber and/or glass fiber. Suitable polymerization processes are those found in U.S. Pat. No. 9,169, 356 B2 and by Laskoski, M.; Dominguez, D. D.; Keller, T. M.; Synthesis and Properties of a Liquid Oligomeric Cyanate Ester Resin, Polymer, 2006, 47, 3727-373

The process of Paragraph 0023 wherein said monomer is combined with a second monomer, said second material, not being produced by a process according to the processes of Paragraphs 0016 through 0022, and then polymerizing said monomers, preferably said second material is selected from the group consisting of cyanate esters, epoxy compounds, oxetanes, phthalonitriles, benzoxazines acrylates and mixtures thereof.

A process of making a plane, missile, space vehicle or consumer product comprising:
  a) incorporating a substrate into said plane, missile, space vehicle, a printed circuit board, (for example the printed circuit's matrix material) or consumer product, preferably said substrate comprises carbon fiber and/or glass fiber; preferably said substrate is a structural component of said plane, missile, space vehicle or consumer product and preferably said plane is a jet;
  b) producing a monomer according to Paragraphs 0016 through 0022 and applying said monomer to said substrate, or applying a monomer produced according to Paragraphs 0016 through 0022 to said substrate before or after said substrate is incorporated into said plane, missile, space vehicle or consumer product, preferably said monomer is combined with a second material before, during or after said monomer is applied to said substrate and said second material is selected from the group consisting of cyanate esters, epoxy compounds, oxetanes, phthalonitriles, benzoxazines acrylates and mixtures thereof; and
  c) polymerizing said monomer before or after said substrate is incorporated into said plane, missile, a space vehicle, (for example a satellite, rocket or space station) or consumer product.

A non-limiting schematic of one embodiment of a microfluidic flow apparatus to carry out the processes of Paragraphs 0016 to 0022 is depicted in FIG. 1. The microfluidic flow apparatus consists of air tight syringes (1) and (2) connected to a microfluidic flow cell (8). All connections are made using 1/16" O.D. ETFE tubing (5) and (6). Air tight syringe (1) is affixed to syringe pump (3) and air tight syringe (2) is affixed to syringe pump (4). Check valves (7) and (8) separate air tight syringes (1) and (2) from a microfluidic flow cell (9). The output from microfluidic flow cell (9) is transported to site (10) for reaction quenching.

Figure 2:
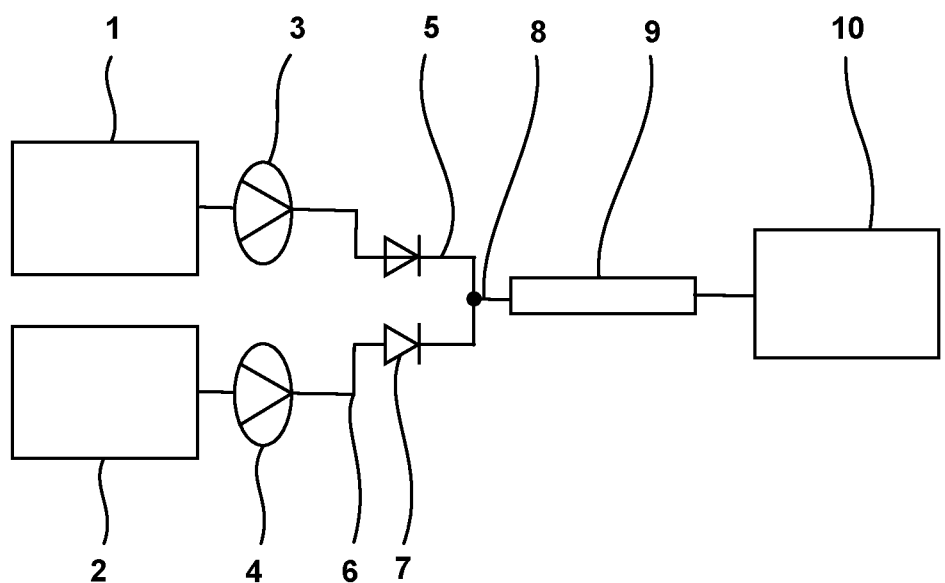
FIG. 2 is a schematic displaying a flow reactor system utilizing a packed-bed reactor.

A non-limiting schematic of one embodiment of a microfluidic flow apparatus to carry out the processes of Paragraphs 0016 to 0022 is depicted in FIG. 2. The microfluidic flow apparatus consists of air tight syringes (1) and (2) connected to a packed-bed reactor (9). All connections are made using 1/16" O.D. ETFE tubing (5) and (6). Air tight syringe (1) is affixed to syringe pump (3) and air tight syringe (2) is affixed to syringe pump (4). The two solutions from syringes (1) and (2) combine in a T-junction (8) or directly into the packed-bed reactor (9). It is important to minimize the volume between where the two solutions first mix and when they enter the packed-bed reactor. Check valves (7) and (8) separate air tight syringes (1) and (2) from the junction (8). The output from the reactor (9) is transported to site (10) for reaction quenching.

Suitable flow reactors to carry out the processes of Paragraphs 0016 to 0022 may be purchased from vendors such as Little Things Factory GmbH of Elsoff, Germany. Packed bed reactors can be constructed from stainless steel tubing with outer diameters ranging from 1/8" to 1/2' with an optimal O.D. of 1/4'. Suitable materials for making such monomers via such processes can be obtained from Sigma Aldrich of St. Louis Mo. USA and resveratrol can be obtained from Evolva San Francisco of Larkspur, Calif. USA.

EXAMPLES

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Example 1. The microfluidic flow apparatus consists of two reagent solutions in 5 mL air tight syringes connected to a microfluidic flow cell of 100 uL internal volume (FIG. 1). All connections are made using 1/16" O.D. ETFE tubing. To a gas-tight syringe, 5 mL of a solution of Bisphenol E (0.25M) and triethylamine (0.525M) in dichloromethane (DCM). Bisphenol E is an aromatic phenol with phenol functionality of 2. An aromatic phenol with phenol functionality of 2 or greater can be used. Examples of such aromatic phenols include bisphenol A, bisphenol S and resveratrol. In a second 5 mL syringe was placed a solution of cyanogen bromide (0.55M) in DCM. Syringes were affixed to syringe pumps. Tubing was connected to syringes according to the configuration in FIG. 1. Microfluidic flow cell was connected to a recirculating chiller set at −40° C. Solution A and solution B were pumped at 600 μL/min giving a reaction residence time of 3 seconds. Reaction product was quenched in 100 mL of deionized water. The organic layer was collected and washed with 100 mL of deionized water, dried over 1.0 g of $MgSO_4$ with stirring, and concentrated by rotary evaporation at room temperature and a pressure of 10 millitorr.

Example 2. The microfluidic flow apparatus consists of two reagent solutions in 5 mL air-tight syringes connected to an assembled packed-bed reactor (FIG. 2). All connections are made using 1/16" O.D. ETFE tubing. Solution A consists of an aqueous solution with the sodium salt of the phenol and small amount of phase-transfer agent, which was prepared by dissolved bisphenol E (0.3932 g) in 9.60 mL of 0.3725 M NaOH solution and adding 12.8 uL of trimethylamine (0.05 eq). The packed bed reactor was placed in a cooling bath and the temperature was maintained under 0° C. Solution B, consisting of 13.65 mL of 0.5 M of cyanogen bromide in dichloromethane, was pumped at 0.48 mL/min and solution A was pumped at 0.4 mL/min giving a retention time of 20 seconds. The organic phase was separated from the aqueous phase and concentrated to afford product.

Example 3. Same as Example 1 except the multifunctional aromatic phenol used was Bisphenol A.

Example 4. Same as Example 1 except solution A consisted of a 0.167 M solution of resveratrol with 0.525 M triethylamine in DCM.

Example 5. Same as Example 1 except the multifunctional aromatic phenol used was Bisphenol S.

Example 6. Same as Example 1 except solution A consisted of a 0.25 M solution of Bisphenol E with 0.525 M triethylamine in acetonitrile (MeCN).

Example 6. Same as Example 1 except solution A consisted of a 0.25 M solution of Bisphenol E with 0.55 M cyanogen bromide in MeCN, and solution B consisted of a 0.525 M solution of triethylamine in acetonitrile.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A process of making a monomer said process comprising processing, in a microfluidic reactor the following materials:
   a) a multifunctional phenol;
   b) a cyanogen halide comprising chloride cyanogen and/or cyanogen bromide; and
   c) a base selected from the group consisting of an organic base, an inorganic base and mixtures thereof;
   at a temperature of from about −78° C. to about 0° C., said materials having residence time of from about 1 second to about 80 seconds.

2. The process according to claim 1, wherein said temperature is from about −40° C. to about −10° C. and said residence time is from about 20 seconds to about 30 seconds or said residence time is from about 1 second to about 10 seconds.

3. A process of making a monomer said process comprising processing, in a microfluidic reactor the following materials:
   a) a multifunctional phenol comprising 1,1-Bis(4-hydroxyphenyl)ethane;
   b) a cyanogen halide; and
   c) a base comprising sodium hydroxide and/or triethylamine;
   at a temperature of from about −78° C. to about 25° C., said materials' having residence time of from about 0.1 seconds to about 600 seconds
   said process comprising combining:
      (i) a first solution comprising a material selected from the group consisting of said multifunctional phenol comprising 1,1-Bis(4-hydroxyphenyl)ethane; and said base comprising sodium hydroxide and/or triethylamine; and
      (ii) a second solution comprising a cyanogen halide;
   b) combining
      (i) a first solution comprising said multifunctional phenol comprising 1,1-Bis(4-hydroxyphenyl)ethane, a cyanogen halide, and an optional aprotic co-solvent selected from the group consisting of dichloromethane, acetonitrile and mixtures thereof; and
      (ii) said base comprising sodium hydroxide and/or triethylamine with the proviso that when said base is a solid base, said solid base is dissolved in a liquid prior to combining said solid base with said first solution; or
   c) simultaneously combining a first solution comprising said multifunctional phenol comprising 1,1-Bis(4-hydroxyphenyl)ethane, acetonitrile and an optional aprotic co-solvent selected from the group consisting of dichloromethane, acetonitrile and mixtures thereof; a second solution comprising a cyanogen halide, and an aprotic solvent selected from the group consisting of dichloromethane, acetonitrile and mixtures thereof; and a third solution comprising said base comprising sodium hydroxide and/or triethylamine with the proviso that when said base is a solid base, said solid base is dissolved in a liquid prior to combining said solid base with said first solution, and an optional aprotic solvent selected from the group consisting of dichloromethane, acetonitrile and mixtures thereof.

4. The process according to claim 3, wherein said cyanogen halide comprises a chloride cyanogen and/or cyanogen bromide.

5. A process of making a monomer said process comprising processing, in a microfluidic reactor the following materials:
   a) a multifunctional phenol selected from the group consisting a 1,4-benzenediol, 1,3-benzenediol, 1,2-benzenediol, 2,2-Bis(4-hydroxyphenyl)propane, 1,1-Bis(4-hydroxyphenyl)ethane, 2,2-Bis(4-hydroxy-3-methylphenyl)propane, 2,2-Bis(4-hydroxyphenyl) hexafluoropropane, 3,4',5-Trihydroxy-trans-stilbene 3,4',5-Trihydroxy-cis-stilbene, 1,1-Bis(4-hydroxyphenyl)sulfone, phenylbis(4-hydroxyphenyl)phosphine oxide, phenylbis(3-hydroxyphenyl)phosphine oxide, tris(3-hydroxyphenyl)phosphine oxide, and mixtures thereof;
   b) a cyanogen halide selected from the group consisting of cyanogen chloride, cyanogen bromide and mixtures thereof;
   c) an inorganic base selected from the group consisting sodium hydroxide, lithium hydroxide, and mixtures thereof;
   d) a base comprising tetraalkyl ammonium hydroxides, at a temperature of from about −78° C. to about 25° C., said materials having residence time of from about 0.1 seconds to about 600 seconds.

6. The process according to claim 1, wherein:
   a) said multifunctional phenol is selected from the group consisting of 2,2-Bis(4-hydroxyphenyl)propane, 1,1-Bis(4-hydroxyphenyl)ethane, 3,4',5-Trihydroxy-trans-stilbene, 3,4',5-Trihydroxy-cis-stilbene and mixtures thereof;
   b) said cyanogen halide comprises cyanogen bromide;
   c) said inorganic base is selected from the group consisting sodium hydroxide, lithium hydroxide, and mixtures thereof;
   d) said organic base is selected from the group consisting of triethylamine, tetrabutylammonium hydroxide, sodium phenoxide and mixtures thereof.

7. The process according to claim 1 comprising a cyanation reaction.

8. The process according to claim 1 wherein said monomer is a cyanation reaction product.

9. The process according to claim 3, wherein said temperature is from about −78° C. to about 0° C. and said residence time is from about 1 second to about 80 seconds.

10. The process according to claim 9, wherein said temperature is from about −40° C. to about −10° C. and said residence time is from about 20 second to about 30 seconds or said residence time is from about 1 second to about 10 seconds.

11. The process according to claim 3 comprising a cyanation reaction.

12. The process according to claim 3 wherein said monomer is a cyanation reaction product.

13. The process according to claim 5, wherein said temperature is from about −78° C. to about 0° C. and said residence time is from about 1 second to about 80 seconds.

14. The process according to claim 13, wherein said temperature is from about −40° C. to about −10° C. and said residence time is from about 20 second to about 30 seconds or said residence time is from about 1 second to about 10 seconds.

15. The process according to claim 5 comprising a cyanation reaction.

16. The process according to claim 5 wherein said monomer is a cyanation reaction product.

* * * * *